United States Patent [19]

Fisher et al.

[11] Patent Number: 4,687,483

[45] Date of Patent: Aug. 18, 1987

[54] HEART VALVE PROSTHESIS

[75] Inventors: John Fisher; David J. Wheatley, both of Glasgow, Scotland

[73] Assignee: University Court of the University of Glasgow, Glasgow, Scotland

[21] Appl. No.: 774,823

[22] Filed: Sep. 11, 1985

[30] Foreign Application Priority Data

Sep. 28, 1984 [GB] United Kingdom ............... 8424582

[51] Int. Cl.⁴ .............................................. A61F 2/24
[52] U.S. Cl. ..................................................... 623/2
[58] Field of Search .................................. 623/2, 900

[56] References Cited

U.S. PATENT DOCUMENTS 2,922,437  1/1960  Rippingille ............................. 623/2
3,574,865  4/1971  Hamaker .
4,470,157  9/1984  Love ....................................... 623/2

FOREIGN PATENT DOCUMENTS 116236  8/1984  European Pat. Off. .

*Primary Examiner*—Richard J. Apley
*Assistant Examiner*—James Prizant
*Attorney, Agent, or Firm*—Pennie & Edmonds

[57] ABSTRACT

A heart valve prosthesis comprising an annular support frame for a plurality of flexible tissue valve components. The support frame has a plurality of spaced posts defining openings therebetween to permit a portion of each valve element to flex from an open position to a closed position. An annular sleeve, concentric with said support frame, is adapted to clamp a non-flexing portion of each valve element in operative position between the support frame and said sleeve.

14 Claims, 7 Drawing Figures

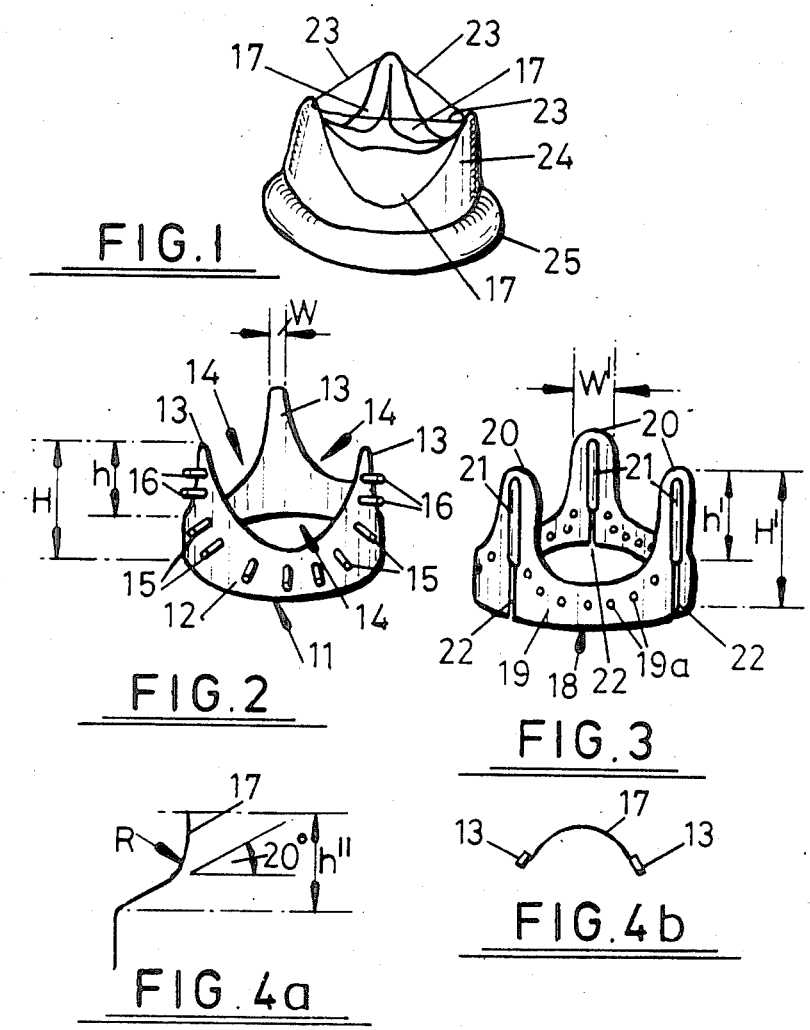

HEART VALVE PROSTHESIS

This invention relates to a heart valve prosthesis. Heart valve prostheses have previously been proposed in a number of forms. An early development in prosthetic heart valves involved the use of various types of mechanical valves such as flap valves or poppet valves. However, heart valve prostheses have utilised three flexible cusps. The cusps are in the form of flexible leaflets which are mounted for flexing about a generally cylindrical base. The leaflets can flex inwardly from the base into a closed position and can flex outwardly to lie in a general cylindrical formation in an open position. Two different types of tissue leaflet valves are commonly manufactured. In one type, complete porcine aortic valves are mounted inside a cylindrical support frame, commonly referred to as a stent. In another type, the leaflets are manufactured from bovine pericardium and also mounted on a frame. Normally the leaflets are mounted on their frame after having been treated with glutaraldehyde which crosslinks and stabilises the collagen in the leaflets and reduces their antigenicity. Materials other than porcine aortic valves or bovine pericardium have been proposed for valve leaflets, for example polyurethane, but valves incorporating leaflets of such other materials are not commercially available for clinical implant at present.

Various forms of frames have been proposed for the foregoing purpose. In, for example, British Patent No. 1,598,112, there is disclosed a heart valve prosthesis wherein the frame is formed by a frame system having a first frame defining three parallel legs on which the leaflets are mounted. A second frame cooperates with the first frame in order to clamp the leaflets therebetween so that the leaflets can be secured to and between the frames.

In European Patent Publication No. 0051451A a heart valve prosthesis is shown in which a frame having a cylindrical base from which extends three integral upstanding legs is formed of a biologically compatible metal or plastic material. Three cooperating valve leaflets are mounted on the frame and are secured to the cylindrical base and to the upstanding legs by stitching. Stitches, referred to as coaptation stitches, secure each leaflet to the upper end of each leg in order to try to ensure that the leaflets deflect inwardly to enable the three leaflets to cooperate together to close the passage through the valve. The frame is covered with a cloth in order to achieve well known biological advantages. The cloth also facilitates the fixing of an annular sewing ring to the outside of the prosthesis.

The above-described previously proposed arrangements have been found to be satisfactory in operation but because of their relatively complex construction and assembly, which involves sewing or the like in order to secure the leaflets to the frame, they have disadvantages in that they do not readily lend themselves to mass production techniques and are consequently relatively expensive to produce. The durability of these valves is not ideal. Mechanical failures and tears in the leaflets have been reported in the short term and biological effects such as calcification can cause valve malfunction in the longer term.

An object of the present invention is to provide a stent for a heart valve prosthesis in which some of the foregoing disadvantages are obviated or mitigated.

According to the present invention there is provided a heart valve prosthesis comprising an annular support frame for a plurality of flexible tissue valve elements, said support frame having a plurality of spaced posts defining openings therebetween to permit a portion of each valve element to flex from an open position to a closed position, and means for securing the valve elements to the support frame characterised in that the means for securing the valve elements to the support comprises an annular sleeve concentric with said support frame adapted to clamp a non-flexing portion of each valve element in operative position between the support frame and said sleeve.

Preferably, the annular support is provided with a plurality of radially extending projections on which the valve elements and sleeve can be mounted to clamp the valve elements in their operative position.

Preferably also, the profile of the clamping sleeve substantially corresponds to the profile of the annular support.

An embodiment of the present invention will now be described by way of example, with reference to the accompanying drawings, in which:

FIG. 1 is a perspective view of a heart valve prosthesis in accordance with the present invention incorporating an inner frame and an outer support sleeve securing a valve tissue provided by three valve leaflets therebetween. The prosthesis is provided with an outer cloth covering and an annular sewing ring;

FIG. 2 is a perspective view of the inner frame;

FIG. 3 is a perspective view of the outer support sleeve;

FIGS. 4a and 4b are diagrammatic representations illustrating vertical and horizontal sections of a valve leaflet;

Figure 5:
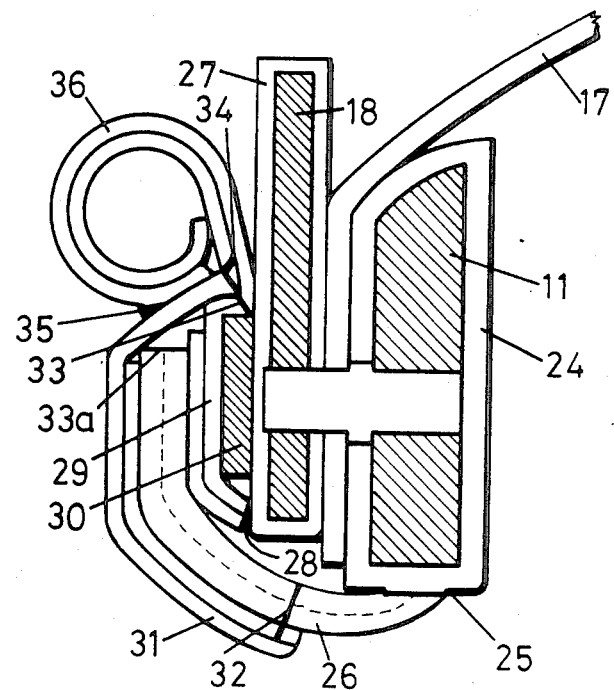
FIG. 5 is a fragmentary vertical sectional view, to an enlarged scale, of a portion of the prosthesis illustrating the manner in which each valve leaflet is supported between the frame and the outer support sleeve.
Figure 6:
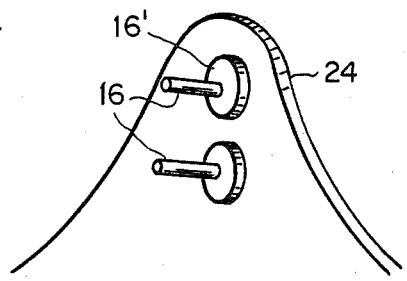
FIG. 6 is a perspective view of the securing washers engaging the studs in order to secure the tissue.

The prosthetic valve is intended for the atrioventricular or ventricular-aortic positions within a human heart and can have a range of sizes of from 25 to 33 mm. diameter for the mitral position and 19 to 27 mm. diameter for the aortic position. The prosthesis as illustrated in the accompanying drawings comprises an inner frame 11 of any suitable biologically inert metal or synthetic plastics material, e.g., acetal. The frame 11 comprises a cylindrical base 12 from which extend upwardly towards the outflow end of the valve three spaced posts 13 integral with the base 12 and which posts define scalloped spaces or sectors 14 therebetween. The outer peripheral edges of the base 12 and posts 13 defining the scallops 14 are bevelled. Mounted in the frame 11 so as to project radially outwardly from the cylindrical base 12 are a plurality of, e.g., seven, tissue-locating pins or similar projections 15. It will be appreciated that the pins 15 do not project radially inwardly beyond the inner surface of the frame 11. From each post 13, a pair of studs 16 extend radially outwardly therefrom and securing washers 16' are engaged with said studs in order to secure a tissue therebetween.

A tissue formed of bovine pericardium or any other suitable natural or synthetic material is utilised to form three valve leaflets 17. The three leaflets 17 are secured to the inner frame 11 by affixing the leaflets 17 on to the seven outwardly projecting pins 15 and two studs 16. The perimeter of each scallop 14 is defined by the intersection of a sphere of approximately 11 mm. radius with the cylindrical base 12 of frame 11. As indicated in FIG. 2, the width W of the tip of the posts 13 is approximately 2 mm., the scallop depth h is 14 mm. and the overall height H of the frame is 18 mm. The internal diameter of the frame 11 is approximately 23 mm. and its outside diameter approximately 25 mm.

An outer support sleeve 18, which is of a suitable flexible biologically inactive material, e.g., acetal, is adapted to be positioned over the external surface of the adjoining leaflets and secured over the outer ends of the pins 15 in order to clamp the lower portion of the leaflets 17 between the inner frame 11 and the outer sleeve 18. Once again, it will be appreciated that the pins 15 do not extend beyond the outer surface of the outer sleeve 18. The outer sleeve 18 has a cylindrical base 19 provided with a series of holes 19a adapted to register with the pins 15 of frame 11. The sleeve 18 also has spaced upstanding posts 20 similar to corresponding portions of the inner frame 11 so that the profiles of the frame 11 and outer sleeve 18 are generally in register with each other when they are located in their operative positions relative to one other. The outer sleeve 18, however, is provided with posts 20 which are broader than those of the inner frame 11 in a circumferential direction and each has a vertical slot 21 adjacent the overlapping region and into which slots the studs 16 and their associated securing washers 16' project. The cylindrical base 19 of the outer sleeve 18 is also provided with vertical slits 22 at the location of each post to enable the cylindrical base 19 of the outer sleeve 18 to be sufficiently distorted to allow it to be easily clipped in position around the base 12 of the inner frame 11 to which the leaflets 17 have been affixed.

The base of the scallop of the outer frame 18 projects 1 mm. above the base 12 of inner frame 11 and the top of the posts 20 project about 2 mm. above their associated posts 13 of the frame 11. As indicated in FIG. 3, the overall height H' of outer sleeve 18 is 20 mm. and the scallop depth h' is 15 mm. The outside diameter of the outer sleeve 18 is 27 mm. and the internal diameter is about 26 mm. The width W' of each post 20 at its upper tip is 7 mm. and the vertical slots 21 are approximately 2 mm. wide.

As shown in FIG. 4a in vertical section, one suitable form of each leaflet 17 at its flexible portion above the base 12 of frame 11 defines an initial angle of about 20° before curving through a radius R of about 11 mm. to extend towards its free edge in a substantially vertical direction. The height h" of the leaflet is approximately 15 mm. FIG. 4b shows the arcuate form of each leaflet when operatively located between its associated posts 13. Each leaflet 17 is preferably manufactured from bovine pericardium selected from specific areas of pericardial sac to give uniform thickness and extensibility. In manufacture of each leaflet it is positioned in a mould and placed in a glutaraldehyde bath to crosslink the tissue and produce the desired geometry for the leaflets. Holes for positioning each leaflet 17 on the pins 15 and studs 16 of the frame 11 are also made when each leaflet is on the mould.

It will be noted that the tips of the posts of the outer sleeve 18 are rounded in order to reduce the risk of myocardial injury in the atrio-ventricular position.

FIG. 5 illustrates, to an enlarged scale, the manner in which, in practice, the sleeve 18 and frame 11 engage and support a valve leaflet 17. Prior to assembly, the frame 11 is enclosed in a covering 24 formed from a single piece of pericardial tissue. The tissue covering 24 is stitched at 25 to provide a double-layer tail 26 of tissue extending therefrom. It will be noted that the inner face of the frame 11 is seamless. The sleeve 18 is covered with a covering 27 of a cloth such as polyester which is stitched at 28 to provide a double-layered extension in the form of a cloth tail 29.

On assembly of the prosthesis of the invention, valve leaflets 17 are positioned on the outwardly extending pins 15 and studs 16 of the tissue-covered inner frame 11, the leaflets being secured to each other by vertical stitched seams at their adjacent edges and tips. Securing washers 16' are then releasably affixed to the studs 16 to secure the leaflets 17 thereto. The cloth-covered outer sleeve 18 is then positioned, as shown in FIG. 5, on the outside of the mounted leaflets 17 on the pins 15 and base 19 of the outer sleeve 18 is secured on to the inner frame 11 by means of a surrounding acetal locking or clamping ring 30, the vertical edges of leaflets 17, the studs 16 and associated securing washers 16' being accommodated within the slots 21 (FIG. 3) of the outer sleeve 18. In this way, each valve leaflet 17 can be mounted accurately and securely in their desired position without the necessity for highly skilled suturing. The clamping of the tissue between the cloth-covered sleeve 18 and tissue covered frame 11 provides an even distribution of pressure on each valve leaflet 17 at its base regions and the studs 16 towards the top of the posts 13 will precisely locate the leaflets 17 thereon. In addition, the outer sleeve 18 protects the pericardial tissue against injury during insertion of the prosthesis and also against possible injury from long suture ends in the aortic position.

As shown in FIG. 5, an external double-layer cloth panel 31 is secured by stitching at 32 to the tissue tail 26.

The cloth tail 29 of the cloth covering 27 of the outer sleeve 18 is folded upwardly over the outer face of locking ring 30 and the inner layer of tail 29 is secured by stitching at 33 along the upper edge of said ring. The tissue tail 26 and cloth panel 31 are subsequently folded upwardly over the secured tail 29 stitched at 33a. The outer layer of the cloth panel 31 is stitched at 34 to the inner layer of tail 29. The tissue tail 26 extends outwardly around the base of the valve to prevent host tissue ingrowth into the valve orifice. The outer layer of panel 31 and inner layer of tail 29 are continued upwardly and wound in a spiral and stitched at 35 to outer layer of panel 31 to form a sewing ring 36 whereby the prosthesis can be secured in its operative position. It will be apparent that the position of the sewing ring relative to the prosthesis can be varied as required in order to give a higher or lower valve profile as required.

If desired, in the atrio-ventricular position the posts 20 of the outer sleeve 18 can be linked by a connecting suture 23 (FIG. 1) to reduce the chance of snaring of sutures on the posts during insertion.

The prosthesis described above is intended for a 27 mm. atrio-ventricular valve and it will be appreciated that the dimensions can be varied in order to suit requirements and for other valves which have to be employed at other locations.

Although it has commonly been found desirable to provide three valve leaflets in a heart valve prosthesis of the type to which the present invention relates, it will be appreciated that it may be possible to use a number of leaflets other than three e.g., two.

It will be appreciated by those skilled in the art that the beneficial functions of a valve produced in accordance with the present invention depend upon care being taken with respect to a number of parameters, e.g., selection and preliminary treatment of the valve leaflets in accordance with accepted practice.

We claim:

1. A heart valve prosthesis comprising an annular support frame for a plurality of flexible tissue valve elements, said support frame having a plurality of spaced posts defining openings therebetween to permit a portion of each valve element to flex from an open position to a closed position, and means for securing the valve elements to the support frame comprising an outer annular sleeve concentric with said support frame adapted to clamp a non-flexing portion of each valve element in operative position between the support frame and said sleeve characterized in that said support frame and said sleeve are releasably secured to each other by means of a plurality in interengaging projections extending from one of the frame and sleeve member and releasably and connected to the other menber and on which the valve elements are mounted.

2. A prosthesis as claimed in claim 1, in which the projections are formed on the support frame and extend outwardly therefrom to engage holes in the surrounding sleeve.

3. A prosthesis as claimed in claim 1, in which the sleeve is provided with a plurality of integral extensions, each of which is adapted to overlie one of the posts of the support frame.

4. A prosthesis as claimed in claim 3, in which each frame post is provided with a projecting stud or studs on which the valve elements are mounted.

5. A prosthesis as claimed in claim 4, in which each projecting stud is formed on the support frame post and is provided with means for securing a valve element or elements thereto.

6. A prosthesis as claimed in claim 5, in which the securing means is a washer or the like adapted to be releasably clipped on to its associated stud.

7. A prosthesis as claimed in claim 3, in which each sleeve extension has formed therein a slot adapted to receive means for joining adjacent tissue leaflets.

8. A prosthesis as claimed in claim 1 in which the sleeve is provided with a plurality of slits spaced circumferentially from each other and each extending partially along the length of the sleeve, said slits permitting deformation of the sleeve in order to enable releasable interengagement of the sleeve about the support frame.

9. A prosthesis as claimed in claim 1, in which an annular locking ring is provided for location about the external surface of the sleeve in order to retain the sleeve in engagement with the support frame.

10. A prosthesis as claimed in claim 1, in which the support frame is entirely surrounded by a covering of tissue whereby the inner face of the covered support frame is seamless.

11. A prosthesis as claimed in claim 10, in which the base of the frame and the sleeve is covered with a continuous piece of tissue.

12. A prosthesis as claimed in claim 1, in which the sleeve is entirely surrounded by a covering of cloth.

13. A prosthesis as claimed in claim 12, in which the cloth covering has an extension formed into a sewing ring extending around the outer circumference of the prosthesis.

14. A prosthesis as claimed in claim 3, in which the integral extensions of the sleeve are linked by a connecting suture to reduce the possibility of snaring during insertion of the prosthesis.

* * * * *